Figure 1:
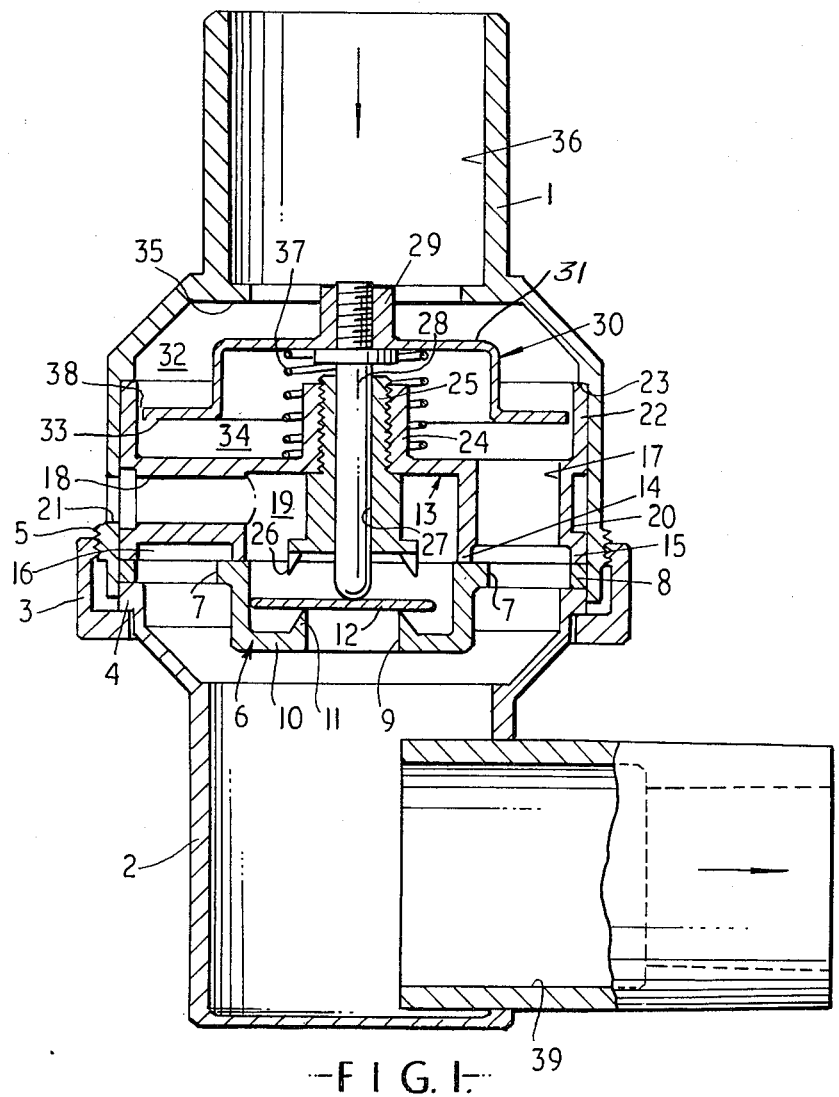

United States Patent [19]
Jones

[11] 3,952,762
[45] Apr. 27, 1976

[54] ANAESTHETIC INFLATION VALVES

[76] Inventor: Wilfred Jones, 155 Bradford Road, Riddlesden, Keighley, Yorkshire, England, BD20 5JH

[22] Filed: May 14, 1974

[21] Appl. No.: 469,634

[30] Foreign Application Priority Data
May 17, 1973 United Kingdom............... 23546/73

[52] U.S. Cl............................... 137/102; 137/494; 137/DIG. 9
[51] Int. Cl.².......................................... F16K 15/14
[58] Field of Search.................. 137/102, 63 R, 529, 137/494, 38, 534, 455, 522, 525.7, 525; 128/145.6, 202, 145.7; 251/65, 61, 231, 331, 336

[56] References Cited
UNITED STATES PATENTS
| | | | |
|---|---|---|---|
| 2,318,721 | 5/1943 | Siver | 137/63 R |
| 3,613,710 | 10/1971 | Oberthur | 137/102 |
| 3,700,000 | 10/1972 | Hesse | 137/494 |

*Primary Examiner*—Martin P. Schwadron
*Assistant Examiner*—Robert J. Miller
*Attorney, Agent, or Firm*—Stevens, Davis, Miller & Mosher

[57] ABSTRACT

An inflation valve comprising an inlet; an inlet valve seat; an inlet valve member having an input face, part of which is engageable with the inlet valve seat, and an output face; a restricted passageway from a first space on the input face side of the inlet valve member to a second space on the output face side of the inlet valve member; an outlet valve seat; an outlet valve member having a first face engageable with the outlet valve seat and capable of being exposed directly or indirectly to pressure in the first or said second space and a second face exposed to exhaust pressure; and a mechanical connection between the two valve members; the mechanical connection and the relationship between the surface areas of the faces being such that when the pressure differential between the first and second spaces is above a given valve the inlet valve is held open and the outlet valve is held closed, but when the pressure differential falls below the given value the outlet valve is opened and the inlet valve is closed.

6 Claims, 3 Drawing Figures

ANAESTHETIC INFLATION VALVES

This invention relates to inflation valves for use in general anaesthesia and resuscitation.

When a patient is under anaesthetic he may be breathing spontaneously, or his breathing may have to be assisted or totally controlled. Anaesthetic systems commonly include a bag in which the gas/air mixture is stored and a patient's breathing can be assisted by the anaesthetist squeezing this bag. If the patient is apneoic then breathing must be totally controlled and a ventilator is used to force the gas/air mixture into the lungs on a regular cycle.

Many different types of inflation valve have been developed to control the flow of the gas/air mixture to the face mask. The main requirement of an inflation valve is that it should allow gas/air mixture to flow to the patient on inhalation, and on exhalation should allow the expired breath to escape to atmosphere. With a number of valves designed to fulfil this function there was a problem of rebreathing, that is not all of the expired breath escaped to atmosphere and some was drawn back into the patients lungs on the next inhalation. This is generally undesirable and inflation valves have been designed to reduce or eliminate the amount of rebreathed gas. While such valves have been generally efficient during spontaneous breathing the number of valves that are satisfactory during assisted or controlled breathing are few, and these suffer from a further disadvantage.

This disadvantage occurs because the valve member that allows expired breath to escape to atmosphere is loaded onto its seat by the circuit pressure of the gas/air mixture coming from the bag, and the pressure of the exhalation must overcome this circuit pressure. The higher the circuit pressure the more tightly are these valve members pressed onto their seats, and these valves tend to lock up. Furthermore, if the fresh gas/air flow exceeds the patient's minute volume it is possible that with such valves the patient's lungs are liable to be inflated to a dangerous level and may even burst.

According to the present invention an inflation valve comprises an inlet; an inlet valve seat; an inlet valve member having an input face, part of which is engageable with the inlet valve seat, and an output face; a restricted passageway from a first space on the input face side of the inlet valve member to a second space on the output face side of the inlet valve member; an outlet valve seat; an outlet valve member having a first face engageable with said outlet valve seat and capable of being exposed directly or indirectly to pressure in said first or said second space and a second face exposed to exhaust pressure; and a mechanical connection between the two valve members; the mechanical connection and the relationship between the surface areas of the faces being such that when the pressure differential between the first and second spaces is above a given value the inlet valve is held open and the outlet valve is held closed, but when said pressure differential falls below said given value the outlet valve is opened and the inlet valve is closed.

A valve according to the invention will not lock up and it is not possible with a normal gas/air supply for the patient's lungs to be inflated to a dangerous level. The valve can be made sufficiently small to incorporate it in a face mask and the amount of dead space in the valve can be small so that rebreathing can be reduced to an extremely low level.

In operation, when gas is being supplied from a bag or ventilator to the inflation valve this gas acts on the input face side of the inlet valve member and causes this to open, the gas then flowing through the restricted passageway to the output face side of the inlet valve member and suffering a pressure drop. This pressure difference persists as long as gas flows from the work outlet connection of the inflation valve to the patient. During this time the pressure on either the inlet or outlet face of the input valve member also acts on the first face of the exhaust valve member. The two valves are mechanically linked and the areas of the various faces are so chosen that the inlet valve member opening force on the input face side is greater than the inlet valve member closing force, which is the sum of the forces on the output face of the input valve member and on the first face of the exhaust valve member. As inspiration is completed the pressures in the first and second spaces tend to equalize and the inlet valve member closing force then exceeds the opening force so that the inlet valve member closes and the exhaust valve member opens, the gas from the patients lungs then flowing to the work outlet connections into the inflation valve and exhausting to atmosphere. It will be appreciated that opening of the exhaust valve is assisted rather than hindered by the circuit pressure once the pressure over the input valve member has equalized and it is this that gives a valve according to the invention its particular advantages.

Preferably the first face of the exhaust valve member is exposed to the pressure in the second space, as a lighter and more compact unit can be made in this way.

Conveniently the inlet valve member is in the form of a disc and the restricted passageway is an annular space between the periphery of the disc and a surrounding wall of a chamber in which the disc moves. Alternatively, or in addition the inlet valve member may be formed with holes therethrough or a restricted passageway may be formed in a connection between the two spaces independent of the inlet valve member.

Figure 2:
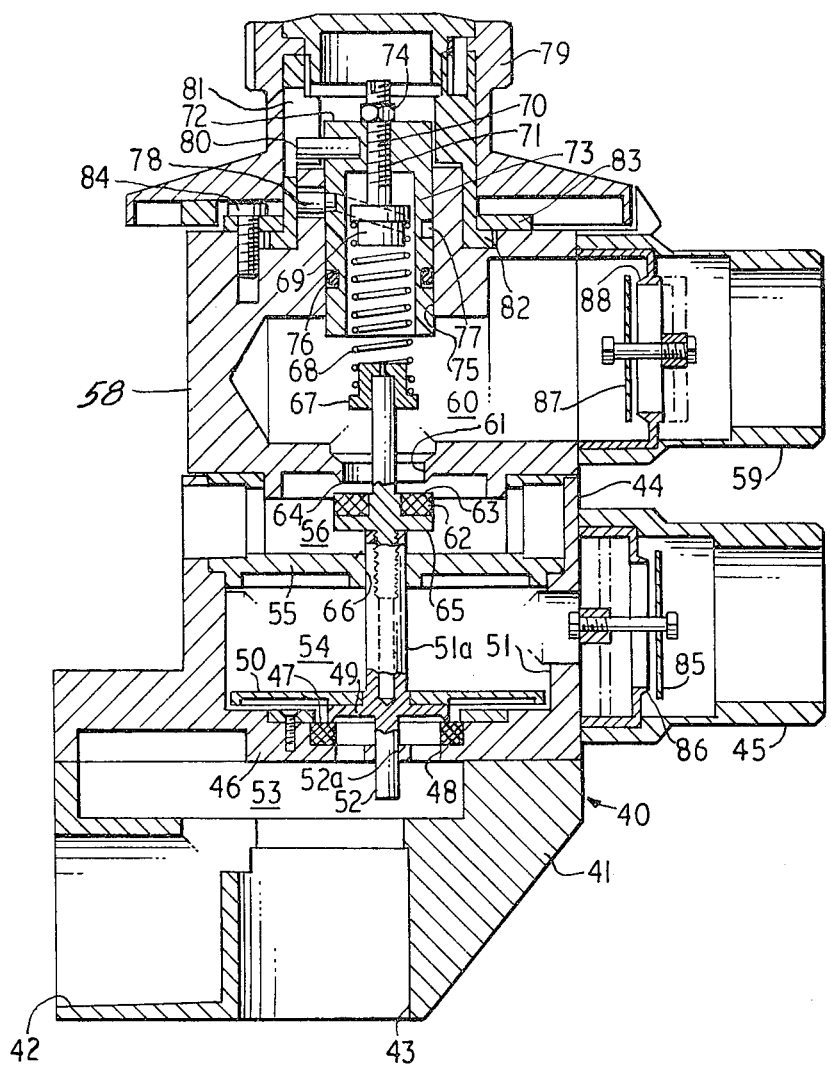
Figure 3:
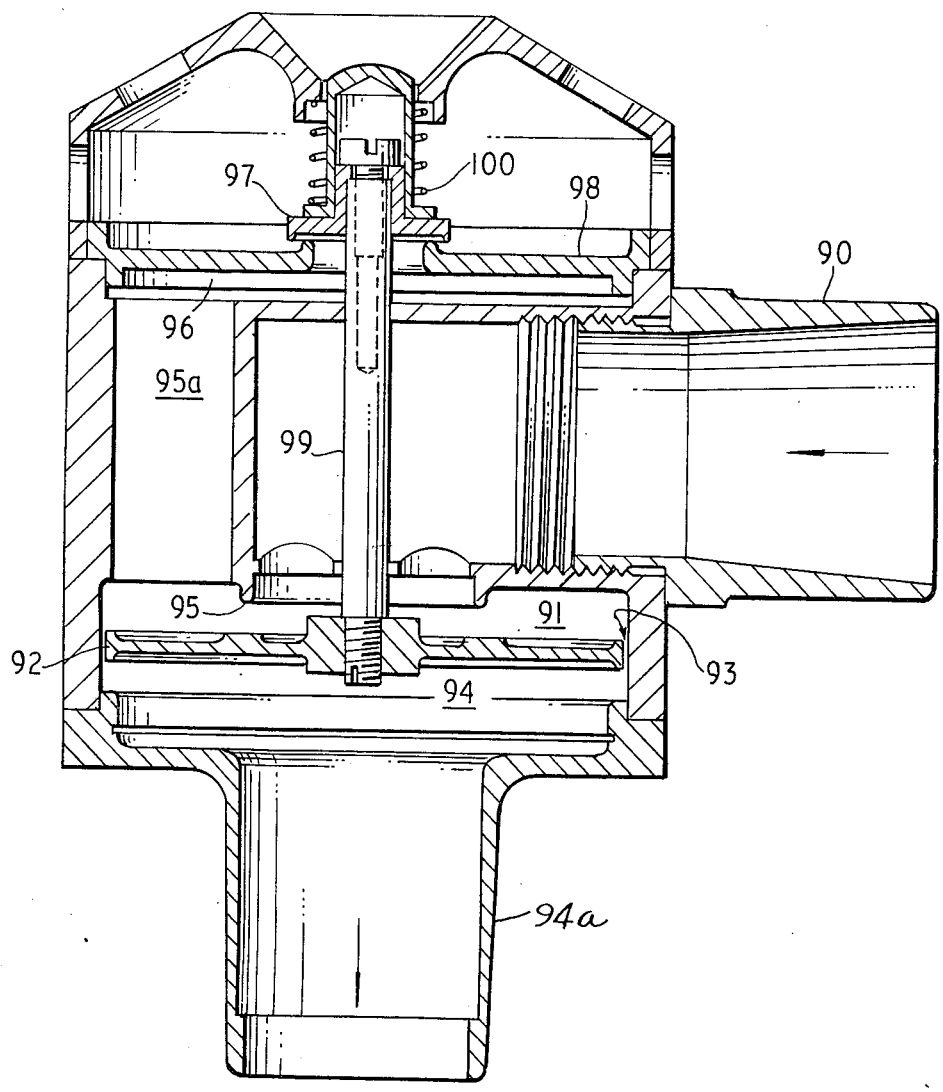

Specific embodiments of inflation valves according to the invention will now be described in more detail, with reference to the accompanying drawings, in which:

FIGS. 1 to 3 are each a cross-section through one of three different embodiments of inflation valve according to the invention.

Referring now to FIG. 1 this shows a valve comprising a two part housing formed of an upper part 1 and a lower part 2, the parts being held together by a retaining ring 3 engaging under a lip 4 on lower part 2 and screwed on to a threaded section 5 of upper part 1. Located within the housing is a part 6 formed with a number of holes 7 in an annular flange section 8 and formed with a central hole 9 in a closed end 10 of a central cylindrical section. The upper side of the end 10 has a raised rim 11 surrounding the hole 9, the rim forming an exhaust valve seat on which rests an exhaust valve member in the form of a disc 12.

Above the part 6 is a further part 13 formed on its lower surface with two annular rims 14 and 15 which seat on the upper surface of part 6 and define between the rims 14 and 15 and facing surfaces of parts 6 and 13 an annular gas space 16. A number of axially extending holes such as 17 extend through part 13 to the gas space 16. A radial passage 18 is formed through part 13 from a central chamber 19 to a circumferential groove 20 formed around the part 13 and communicating with an exhaust opening 21 in the upper part 1 of the housing.

The parts 6 and 13 are held in their respective axial positions by the action of retaining ring 3 which forces the lower part 2 of the housing against the flange section 8 of part 6, the flange section 8 against the rim 15 and an upper cylindrical section 22 of part 13 against a shoulder 23 on the upper part 1 of the housing.

The part 13 has a central, internally threaded boss 24 into which is screwed a combined guide and stop member 25. Member 25 has four protrusions 26 which act as a stop for exhaust valve disc 12, and an axial bore 27 in which is guided a plunger 28. At its lower end the plunger contacts exhaust valve disc 12 and at its upper end it is screwed into an internally threaded boss 29 projecting from an inlet valve member 30. Inlet valve member 30 has an input face 31 open to a first space 32 on the inlet side of the member 30 and an output face 33 open to a second space 34 on the opposite side of the member 30. Part of the input face 31 can contact a seat 35 to close off flow from an inlet 36. The inlet valve member 30 is biased towards the seat 35 by a compression spring 37. An annular restricted passageway 38 is formed between the edge of the inlet valve member 30 and the inner wall of cylindrical section 22.

A flexible hose may be connected to the inlet 36 to carry pressurized gas/air mixture from a ventilator or bag. The interior of the lower part 2 of the housing has a work outlet connection 39 fitted thereto to which a face mask may be connected.

In operation as gas/air mixture is delivered under pressure to inlet 36 this moves the inlet valve member 30 to the position shown, wherein exhaust valve member 12 is held closed on seat 11 by plunger 28. The incoming gas/air mixture flows from first space 32 through the restricted passageway 38 to second space 34, thereby suffering a pressure drop. From space 34 the mixture flows through holes 17, space 16 and holes 7 to the interior of the lower part 2 of the housing and thence to the work outlet connection 39. When a given volume of gas/air mixture has been delivered to fully inflate the patient's lungs, flow through passageway 38 diminishes and the pressures in spaces 32 and 34 substantially equalize so that the resultant force on inlet valve member 30 due to these pressures falls. However, the face of the exhaust valve member 12 is exposed to the gas/air mixture at substantially the same pressure as that in space 34 and in the lungs, and as this pressure is super-atmospheric the exhaust valve disc 12 will be lifted from its seat so that the patient will expire to atmosphere. As valve disc 12 lifts from its seat the inlet valve member 30 engages seat 35 to close the inlet 36. On the patient's next breath the cycle starts again.

The valve shown in FIG. 2 relies on indirect communication between the output face side of the inlet valve member and the first face side of the exhaust valve member.

The valve comprises a housing 40, the lower section 41 of which is formed with an inlet passage 42 for receiving an anaesthetic gas mixture from an anaesthetic machine and a passage 43 to which a standard rubber reservoir bag may be fitted. Superposed on part 41 of the housing is a further part 44 to which is secured a work outlet connection output member 45 which can be connected by a flexible tube to a face mask applied to a patient. The internal space in parts 41 and 44 of the housing is divided by a web 46 having a valve seat 47 around an inlet duct 48 through the web 46 and an inlet valve member 49 is engageable with the seat 47 to close off the inlet duct. This valve also has a plate element in the form of a disc 50 which is a close fit within a cylindrical section 51 of the web 46. The valve member 49 and disc 50 are carried as an integral unit on a rod 51a having a stem 52 which passes through a guide hole 52a in part of the web 46. In the closed position, the valve member 49 closes off the first space 53 within section 41 of the housing and on the input face side of the inlet valve member, from second space 54 within the part 44 of the housing and on the output face side of the inlet valve member.

A further web 55 within the housing section 44 divides the second space 54 from an exhaust space 56 leading to an exhaust port which can discharge to atmosphere or to a waste gas collector.

Above the housing section 44 is a further section 58 having a work outlet connection input member 59 to which may be connected a flexible tube coming from the face mask for the patient. Gases exhaled by the patient can thus pass to space 60 within section 58 and thence through an exhaust valve port 61 to the exhaust space 56. The exhaust valve port 61 can be closed by an exhaust valve member 62 having a face 63 engageable with an exhaust valve seat 64 and a second face 65 exposed to exhaust pressure. The exhaust valve member 62 is carried by the same rod 51a that carries the inlet valve member 49 and this rod extends through a guide hole 66 in the web 55.

The upper end of rod 51a carries a locating member 67, on which bears one end of a compression spring 68, the other end of which is held by a further locating member 69 mounted on a threaded stem 70. The threaded stem 70 is screwed into a tapped bore 71 formed in a web 72 of a sleeve 73 and the stem 70 is held in the bore by a locknut 74. The sleeve 73 fits within a cylindrical space 75 defined in the upper part of housing section 58 and a sealing ring 76 is provided between the space 75 and sleeve 73. The outer surface of sleeve 75 is formed with a part helical groove 77 in which engages a peg 78 secured to the housing section 58. The sleeve 73 is keyed to rotate with a control element 79 by a peg 80 engaging in an axial slot 81 in the control element. The control element 79 is axially held on the housing by a radial flange 82 located under a retaining plate 83 secured to the section 58 by bolts such as 84.

The work outlet connection output member 45 has mounted therein a non-return flap valve 85 capable of engaging a seating 86. The work outlet connection input member 59 incorporates a further non-return flap valve 87 capable of closing against a seating 88.

To use the valve in totally controlled or ventilated breathing the control element 79 is turned to the required setting, so preloading the spring 68 to control the pressure at which inlet valve member 49 will open. When the gas mixture in the reservoir bag fitted to passage 43 reaches a set pressure the inlet valve member 49 will be lifted from its seat 47 against the spring biasing force. The valve thus partially opens and the restricted clearance between disc 50 and cylindrical section 51 retards an immediate release of gas with the result that the pressure is applied to the larger area of disc 50 to give a greater opening force. This greater force overcomes the increasing closing force due to the spring being compressed and fully opens the inlet valve.

The gas/air mixture thus flows past the valve into space 54 and opens the flap valve 85 to flow into work outlet connection output member 45 and thus to the patient. As the inlet valve opens exhaust valve member 62 closes on to its seat 64 to prevent exhaust of the gas mixture to atmosphere and to ensure that this mixture flows into the patients lungs. As gas flows from the reservoir bag through the inlet valve the pressure in the reservoir bag falls and the pressure in space 60 tends to equalize the pressure in space 54. Consequently the spring 68 will return the inlet valve member 49 to its seating to close off the inspiratory gas flow and the exhaust valve member 62 will open. The pressure in the patients lungs is higher than atmospheric pressure and as the exhaust valve opens there will thus be a flow of the gas mixture from the lungs through flap valve 87 and outlet valve 62 to exhaust. The inlet valve will be held closed and the exhaust valve held open until the pressure in the reservoir bag has once again built up to the required level due to fresh gas flowing into the bag. With a constant fresh gas flow to the bag the valves will thus open and close at regular intervals and a uniform amount of fresh gas will be delivered through inlet valve member 49 to the patient during each open period of the inlet valve.

Communication between second space 54 and the space 60 above the exhaust valve member 62 is, as stated, indirect, being by way of the flexible tubes and face mask, but the principle of operation is the same as valves wherein this communication is direct.

Both valves described so far have had the exhaust valve member exposed to the pressure at the patient outlet of the valve, however, this member may alternatively be exposed to the fresh gas inlet pressure as shown in the embodiment of FIG. 3.

In this arrangement fresh gas flows to an inlet 90 to a first space 91 at one side of an inlet valve disc 92. The gas can then flow through a restricted passageway 93 around the periphery of the disc 92 to a second space 94 and thence to a work outlet connection 94a to the patient. The inlet valve disc 92 may engage a seat 95. The first space 91 communicates by a passage 95a with an upper chamber 96 which is closed by an exhaust valve member 97 on a seat 98. The exhaust valve member and inlet valve disc are connected to move together by a rod 99. A light compression spring 100 biases outlet valve member 97 closed and inlet valve disc 92 open.

Towards the end of an inhalation of fresh gas the pressures over inlet valve disc 92 will become more nearly equal, and the pressure on exhaust valve member 97 will then lift this valve member from its seat and will move the inlet valve disc 92 onto its seat. The patient's exhalation will thus pass exhaust valve member 97 to exhaust.

The spring 100 may be present to ensure that operation occurs at the required pressure differences. Means may be provided for adjusting the spring 100.

In all embodiments of the valve according to the invention the surface areas of the inlet and exhaust valve elements, and any spring loading on these valves is designed so that as long as there is a pressure drop of not less than a certain magnitude from the first side to the second side of the inlet valve then the inlet valve member will be open and the exhaust valve member closed. As the pressure drop falls below this magnitude, however, the resultant force on the two valves will be sufficient to close the inlet valve member and open the exhaust valve member so that the patients lungs empty to exhaust. The exhaust valve member is loaded to its open position by the system pressure so it can not lock up. Over-inflation of the lungs is prevented as pressures over the inlet valve member will equalize when the lungs are fully inflated, so allowing the exhaust valve to open and gas to be expelled from the lungs. The amount of dead space in the valve can be made small in relation to the patient's minute volume so that the amount of rebreathing may be negligible. Obviously any significant amount of rebreathing is prevented as exhaled gas is prevented from entering the tube from the fresh gas supply due to the closure of the inlet valve.

What I claim is:

1. An inflation valve for controlling flow of fluid from an inlet to a work outlet and from the work outlet to exhaust, said valve comprising: an inlet valve seat; an inlet valve member having an input face to which incoming fluid is directed, part of said input face being engageable with said inlet valve seat, and an output face; a restricted passageway connecting a first space on the input face side of the inlet valve member to a second space on the output face side of the inlet valve member; an exhaust valve seat; an exhaust valve member having a first face engageable with said exhaust valve seat and capable of being exposed to pressure in one of said first and said second spaces, and a second face exposed to exhaust pressure; work outlet connection means for receiving input fluid from said second space and for directing fluid for exhaust to said first face of said exhaust valve member; and mechanical connecting means between said inlet and exhaust valve members, said mechanical connecting means and the relationship between the surface areas of said faces of said valve members being such that when the pressure differential between said first and second spaces is above a given value said exhaust valve member is held closed and said inlet valve member is held open to allow fluid to flow from said inlet to said work outlet, but when said pressure differential falls below said given value said inlet valve member is closed and said exhaust valve member is opened to allow fluid to flow from said work outlet to said exhaust.

2. An inflation valve according to claim 1 in which said first face of said exhaust valve member is exposed to the pressure in said second space.

3. An inflation valve according to claim 2 in which said work outlet connection means comprises an output member in communication with said second space, and an input member in communication with a space in which said first face of said exhaust valve member lies, said output member and said input member including means for connecting thereto a flexible tube or tubes leading to a face mask.

4. An inflation valve according to claim 1 in which said inlet valve member is in the form of a disc and said restricted passageway is an annular space between the periphery of said disc and a surrounding wall of a chamber in which said disc moves.

5. An inflation valve according to claim 1 in which said inlet and exhaust valve members are coaxial and said mechanical connecting means is an axially extending rod to which said valve members are secured.

6. An inflation valve according to claim 1 and including resilient means biasing said inlet valve member to a closed position and said exhaust valve member to an open position.

* * * * *